United States Patent [19]

Scheid

[11] Patent Number: 5,040,202
[45] Date of Patent: Aug. 13, 1991

[54] METHOD AND APPARATUS FOR REDUCING X-RAY GRID IMAGES

[75] Inventor: Carl C. Scheid, Delafield, Wis.
[73] Assignee: General Electric, Milwaukee, Wis.
[21] Appl. No.: 361,989
[22] Filed: Jun. 5, 1989
[51] Int. Cl.⁵ ............................................. G21K 1/00
[52] U.S. Cl. ...................................... 378/155; 378/146
[58] Field of Search ........................ 378/14 C, 154, 155

[56] References Cited

U.S. PATENT DOCUMENTS

| | | | |
|---|---|---|---|
| 2,102,146 | 12/1937 | Garretson | 378/155 |
| 3,904,531 | 9/1975 | Barrett et al. | |
| 4,063,100 | 12/1977 | Williams | 250/452 |
| 4,528,685 | 7/1985 | Kump et al. | 378/157 |
| 4,703,496 | 10/1987 | Meccariello et al. | 378/99 |
| 4,744,099 | 5/1988 | Huettenrauch et al. | 378/157 |
| 4,803,716 | 2/1989 | Ammann et al. | 378/155 |
| 4,901,335 | 2/1990 | Ferlic et al. | 378/155 |

FOREIGN PATENT DOCUMENTS

| | | |
|---|---|---|
| 0144670 | 8/1985 | European Pat. Off. |
| 0255017 | 7/1986 | European Pat. Off. |
| 0251407 | 1/1988 | European Pat. Off. |
| WO8701555 | 8/1986 | PCT Int'l Appl. |

Primary Examiner—Craig E. Church
Attorney, Agent, or Firm—Quarles & Brady

[57] ABSTRACT

1. A diagnostic x-ray machine including a reciprocating grid reduces grid lines, in the radiographic image, formed as a result of velocity variations in the reciprocation of the grid, principally at the points of grid reversal. An x-ray source produces a beam of x-ray radiation along a major axis directed through the body and to the grid. A reciprocating mechanism moves the grid within a plane perpendicular to the major axis between a first limit and a second limit and the x-ray beam is modulated synchronously with the grid motion to reduce the grid image at points of grid speed variation.

8 Claims, 3 Drawing Sheets

METHOD AND APPARATUS FOR REDUCING X-RAY GRID IMAGES

BACKGROUND OF THE INVENTION

The field of the invention is x-ray apparatus for diagnostic imaging and in particular x-ray equipment having grids to reject scattered radiation.

Apparatus for creating x-ray radiographs is comprised generally of an x-ray source and an x-ray sensitive medium, such as a photographic film and screen combination, for recording an image produced by the varying transmission of x-rays directed through an imaged body.

The intensity of a radiographic image at any given point on its surface is ideally a function of the absorptive characteristics of the imaged body along a straight line from the x-ray tube to that point on the image. For this relationship to hold, x-rays that have not traveled in a straight line from the x-ray tube to the medium, i.e. those that have been scattered within the body, must be blocked to prevent their contribution to the recorded x-ray image.

Shielding the medium from scattered x-rays is typically done with a grid which is placed immediately above the medium's surface. The grid contains channels that are oriented to pass only rays proceeding in straight lines from the x-ray tube. These channels are formed by rows of parallel vanes which are constructed of an x-ray absorptive material. The vanes are separated by either a low absorptivity solid, such as plastic, or in certain instances by air gaps. Air gapped grids are used preferentially for imagining soft tissue because they attenuate the x-ray beam less and therefore provide greater contrast in the radiographic image.

The physical thickness of the grid vanes, as measured along the plane of the x-ray sensitive medium, cause some of the x-rays that would otherwise be passed by the grid, to be blocked. The blocking of these rays causes shadow "grid lines" in the image. Even fine grid lines may be distracting and larger grid lines may obscure diagnostically significant detail in the image. The problem of grid lines is most severe in grids where the vanes are spaced by air gaps as the vanes of such grids are typically thicker so that they may be self-supporting.

One method of reducing grid lines is to move the grid back and forth in the plane of the x-ray sensitive medium during the time of the x-ray exposure. The grid shadow is thus blurred by falling on different areas of the medium during the x-ray exposure. If the grid can be moved so that each area of the medium is eclipsed by a vane for an equal proportion of the exposure time, the grid lines will be effectively eliminated.

In general it is quite difficult to move the grid so that its vanes spend an equal time over each area of the medium. Reciprocating the grid at a constant speed with respect to the medium surface is one approach. Yet the goal of constant speed is upset when the grid changes direction and must be decelerated then re-accelerated in the opposite direction. With any physically realizable reciprocation, the grid vanes will spend a disproportionate amount of their time near the end of their travel as compared with the center of their travel. Accordingly, faint grid lines may appear under each vane at the vane's point of direction reversal.

SUMMARY OF THE INVENTION

The present invention reduces grid lines formed during periods of changing velocity of the grid vanes by modulating the exposing x-ray beam intensity as a function of the movement of the grid.

According to the invention, an x-ray source produces a beam of x-ray radiation which is directed through the body and which may be controlled in intensity. X-rays scattered by the body are rejected by a reciprocating grid positioned in front of an x-ray sensitive medium. The grid is reciprocated within a plane generally perpendicular to the beam of x-rays and a modulator synchronously controls the intensity of the x-ray beam as a function of the grid reciprocation.

It is therefore a general object of the invention to reduce exposure variations across the x-ray sensitive medium resulting from uneven movement of the reciprocating grid. The intensity of the x-ray beam is decreased when the grid velocity drops so as to counteract the proportionally greater exposure accumulated by the unobscured areas of medium during these times. This counteracting modulation of the x-ray beam provides an even exposure of the x-ray sensitive medium.

It is another object of the invention to provide a simple means for eliminating grid lines produced by velocity changes of the grid at the ends of its reciprocating travel. The x-ray beam is blocked for the short period of time at the ends of grid travel when the grid changes direction to prevent formation of the grid line shadows. In a first embodiment, the x-ray beam is controlled by a chopper wheel, and in a second embodiment the intensity of the x-ray beam is controlled by controlling the x-ray tube voltage.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

The particular system to be described in this section is adapted for use in a fan beam mammography system, however, it should be emphasized that the invention is equally applicable to area beam x-ray systems incorporating movable grids.

Figure 1:
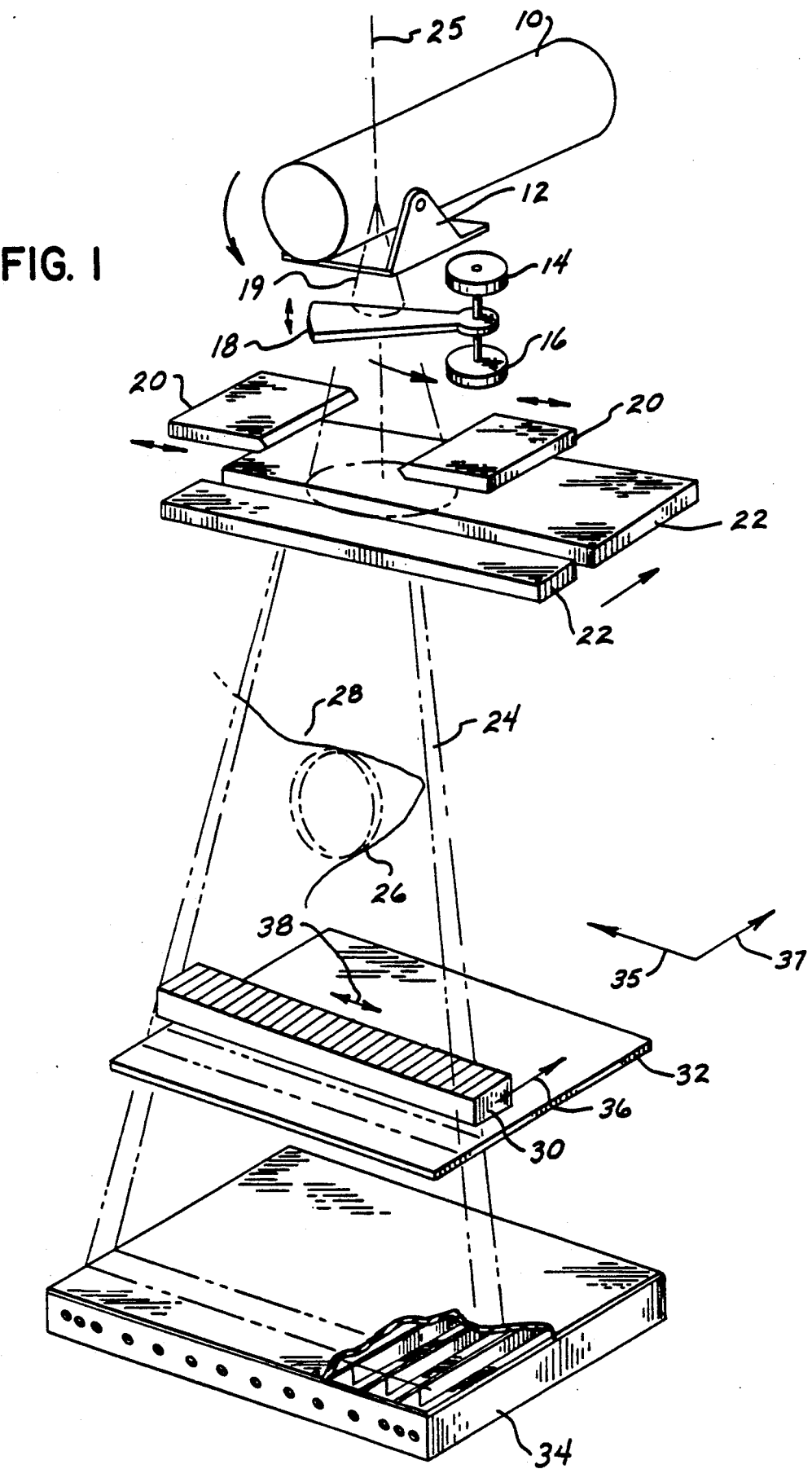
FIG. 1 is a simplified, exploded perspective view of a fan beam x-ray radiograph apparatus showing a chopper wheel and a grid for rejecting scattered x-rays.

Referring to FIG. 1, a radiographic system incorporating the present invention includes an x-ray tube 10 directed to project a beam of x-rays 19 through soft tissue 28 toward x-ray sensitive medium 32. The x-ray beam diverges equally about a major axis 25. X-ray tube 10 may be tipped on tube pivot 12 to sweep the major axis 25 in a longitudinal direction 37 as will be described further below.

A chopper 18 is driven by chopper motor 14 to periodically block the path of the x-ray beam 19 with a radio-opaque vane shortly after its exit from x-ray tube 10. Chopper encoder 16 is coupled to the chopper 18 to permit accurate control of the position of the chopper 18 and hence the timing of the beam occlusions.

The chopper modulated x-ray beam passes through the beam length shutters 20 and beam sweep shutters 22 which collimate the x-rays into a fan beam 24. The beam length shutters 20 are independently adjustable in a transverse direction 35 to control the x-ray fan beam's transverse dimension or length. The beam sweep shutters 22 which define a transverse slit, control the x-ray beam's longitudinal dimension or width. The beam sweep shutters 22 also move together in a longitudinal direction 37 to follow the major axis 25 of the x-ray beam when the x-ray tube 10 is tipped about pivot 12. The tipping of the x-ray tube 10 and the motion of the beam sweep shutters 22 in tandem thereby sweeps the fan beam 24 along the longitudinal axis 37 in synchronization with grid 30, described below.

The fan beam 24 projects through a slice 26 of the imaged soft tissue body 28 and proceeds through grid 30 to project an image of slice 26 on the x-ray sensitive medium 32. The attenuated fan beam 24 passes through the medium 32 and is detected by exposure detector 34 such as that described in co-pending application entitled: "Focused Multielement Detector for X-ray Exposure Control" filed on even date herewith, Ser. No. 07/509,598.

As the fan beam 24 progresses longitudinally across the imaged soft tissue body 28 and across the surface of the medium 32, a continuous projection of the imaged body 28 is formed. As will be described in detail below, the grid 30 translates longitudinally across the surface of the medium 32 to follow the sweeping fan beam 24 and simultaneously reciprocates transversely as indicated by arrows 38 to reduce the formation of grid lines on the medium 32.

Figure 2:
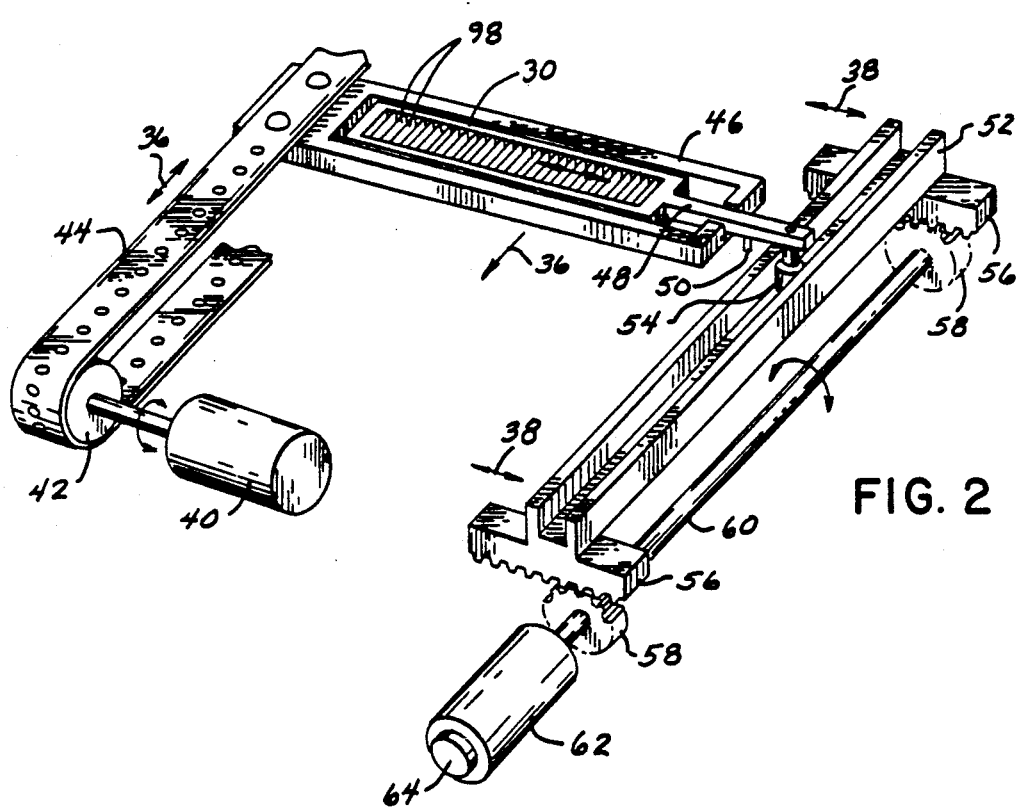
FIG. 2 is a cut-away perspective view of the mechanism supporting the grid of FIG. 1.
Figure 6:
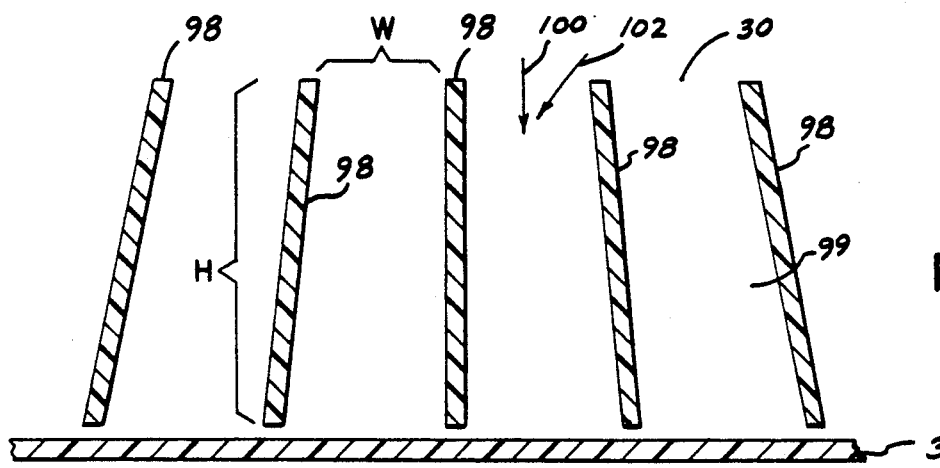
FIG. 6 is a simplified sectional view of the grid of FIG. 1 taken along lines 6—6 of FIG. 2.

Referring generally to FIGS. 2 and 6, the grid 30 is composed of a series of x-ray absorbing vanes 98 which are spaced apart in the transverse direction and which are aligned or "focussed" to the x-ray tube 10. The vanes 98 form channels 99 of width w and of height h which prevent scattered x-rays from reaching the medium 32, as has been described. Referring to FIG. 6, for example, ray 100 arriving directly from x-ray tube 10 may pass between the vanes 98 to strike the medium 32. Ray 102, however, which enters the grid 30 obliquely after having been scattered by a structure within the imaged body 28 (not shown) is absorbed by vane 98' prior to striking the surface of the medium 32. The ratio of the grid height to the grid width is termed the grid ratio and the higher the grid ratio, the stronger the "focussing" effect of the grid, i.e., the more nearly perpendicular to the surface of the medium the rays must be to pass unobstructed.

Referring again to FIG. 2, grid 30 may reciprocate in a transverse direction 35 within a generally rectangular grid reciprocation guide 46. Guide 46 is positioned on top of film cassette 68, which contains x-ray sensitive medium 32, and which in turn is positioned above exposure detector 34. Cassette 68 provides a means of conveniently changing the medium as is generally understood in the art. A lead impregnated belt 66 whose width is equal to the length of the grid reciprocation guide 46, attaches to one upper transverse edge of the grid reciprocation guide 46 and forms a loop which wraps around the film cassette 68 and the exposure detector 34 and back to the remaining upper transverse edge of the grid reciprocation guide 46. The medium 32 is thus shielded from the fan beam 24 except as may be admitted through the grid 30 held in the grid reciprocation guide 46.

Attached to one edge of the lead belt 66 is drive belt 44 which is driven by sprocket wheel 42 so as to move belt 66 and hence grid reciprocation guide 46 and grid 30 in the longitudinal direction 36 to follow the sweeping fan beam 24 when the sprocket wheel 42 is rotated. Belt guides 47 provide surfaces to support the belt 66 as it moves around the film cassette 68 and exposure detector 34. The moving grid 30 and belt 66 are isolated from the imaged body 26 by radiolucent lower compression plate 70 which forms the top surface of enclosure 72.

Figure 3:
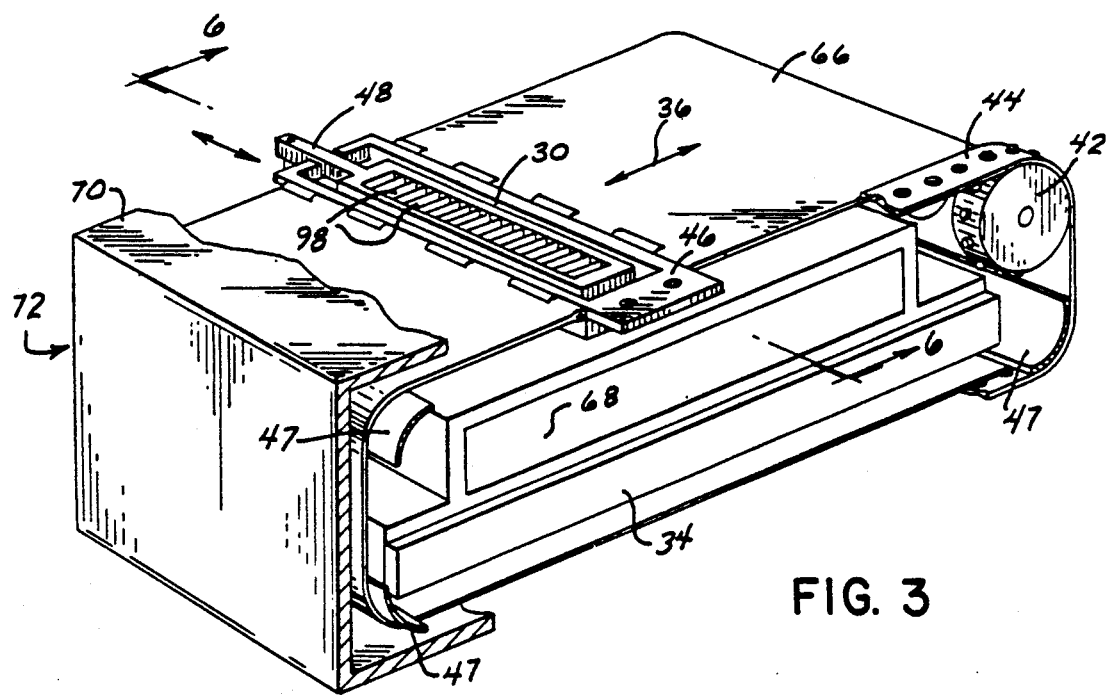
FIG. 3 is a perspective view of the grid control mechanism with the belt removed and orientated to show the reciprocation motor assembly.

Referring to FIG. 3, sprocket wheel 42 is driven by sweep motor 40 which is synchronized to the sweeping of the fan beam 24 so as to hold the guide 30 within the fan beam as it sweeps longitudinally across the surface of the medium 32. During the longitudinal sweeping motion of the grid reciprocation guide 46 and hence the grid 30, the grid 30 is reciprocated transversely by reciprocation arm 48. A follower 54, attached to the free end of the reciprocation arm 48 fits within longitudinal reciprocating track 52 which is orientated to allow the grid 30 and reciprocation arm 48 to move in a longitudinal direction while maintaining contact with the reciprocating track 52 through the follower 54. Attached to each end of the reciprocation track 52 are racks 56 fitted in turn to pinions 58 which move the reciprocating track 52 back and forth in the transverse direction 35 when the pinions 58 are rotated back and forth. The rotation of the pinions 58 is accomplished through a pinion drive shaft 60 by means of reciprocation motor 62. Attached to reciprocation motor 62 is a position encoder 64 which produces precise position feedback information regarding the reciprocation of the grid 30.

Figure 7:
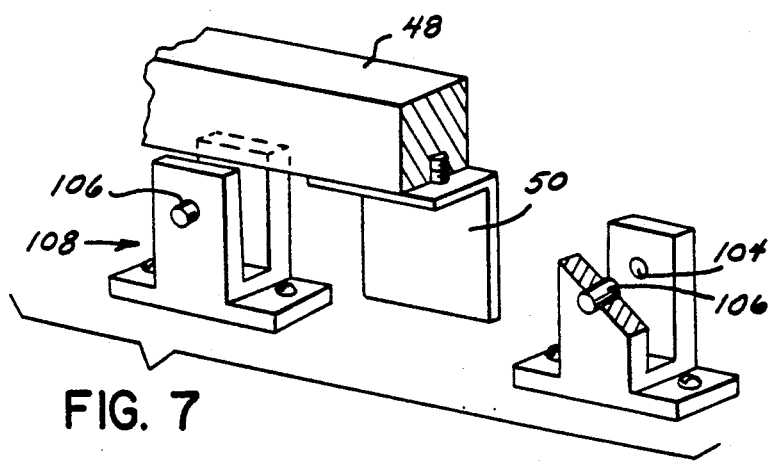
FIG. 7 is a perspective view of an optical interrupter assembly for controlling the modulation of the x-ray beam, with portions of the assembly removed to show the relative positioning of the assembly's elements.

Extending from the lower surface of the reciprocation arm 48 is metal finger 50. Referring to FIG. 7, the metal finger 50 serves alternately to interrupt the light beam of one of two optical interrupters 108. Each optical interrupter contains a light emitting diode 104 and a semiconductor photo-detector 106 which operate together to produce a signal when the metal finger 50 has reached either of two reference points 112 in its reciprocating motion 38 prior to the ends of its reciprocating travel 110. As will be described below, the x-ray beam may be stopped during the time the metal finger 50 blocks either optical interrupter 108. In this case, the metal finger 50 is adjusted to interrupt the optical interrupters 80 during grid reversal, that is, the distance in the grid's reciprocation when the vane 98 motion is not constant. The distance between the reference point 112 and the end of the reciprocating travel 110 determines by what percentage the x-ray exposure will be reduced. As will be apparent to one skilled in the art, this percentage may be adjusted by changing the position and width of the finger 50 and the distance between the optical interrupters 108.

Figure 4:
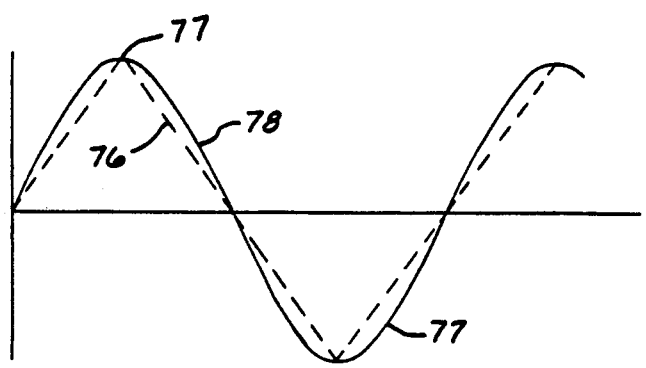
FIG. 4 is a diagram showing the motion of the reciprocating grid with respect to the medium and in particular showing the grid's ideal and actual trajectory.

Referring generally to FIGS. 4 and 6, the grid 30 reciprocates in a transverse direction 35 approximately 12 channel widths w while it translates, in the beam sweep direction 36, a distance equal to the longitudinal length of the vanes 98, that is, the effective width of the fan beam 24 in the longitudinal direction. Synchronization of the grid 30 reciprocation and the beam sweep speed reduces variations in exposure resulting from the modulation of the x-ray beam as will be discussed further below.

During a given cycle of grid reciprocation, approximately twelve vanes 98 pass over each area of the medium surface 32. The exact distance traveled by the grid is not critical, however, because reciprocating the grid by more than one channel width w eliminates the need to reciprocate the grid by an integer multiple of channel width w. This may be understood by considering a grid 30 which moves somewhat less than twelve grid spacings during its reciprocation. Some points on the surface of the medium 32 will be passed over by only eleven vanes during a grid motion cycle. The variation in exposure between these points and those which are passed over by a full twelve grid vanes are generally not noticeable and may be further reduced by moving the grid 30 additional distance during each cycle.

Referring to FIG. 4, the ideal trajectory of the grid is a triangle wave 76. Such a trajectory is of constant velocity and therefore causes the grid vanes to shadow each area of the medium 32 for an equal amount of time, eliminating grid lines. The triangle wave trajectory 76, however, is physically impossible to achieve because it requires instantaneous direction reversal of the finite mass of the grid 30. Waveform 78 is representative of an achievable grid trajectory, being essentially a triangle wave with rounded peaks and valleys 77 representing the deceleration and acceleration of the grid mass. It is during these times of acceleration and deceleration 77 that grid lines will be formed on the medium 32.

The uneven exposure of the medium during grid turn around time can be eliminated by interrupting the x-ray exposure during the grid turn around time. In a practicable system, the turn around time of the grid may be less than 5% of the period of the grid reciprocation. Therefore, if the grid cycle takes one second, interrupting the exposure for 50 ms. will eliminate the grid lines.

The beam 24 may be interrupted or modulated, as will be described below, by chopper wheel 18 which is synchronized with the grid motion by means of the signal generated by the position encoder 64 attached to the reciprocation motor 62. In a second embodiment, the x-ray beam 24 is modulated by reducing the voltage to the x-ray tube 10 when finger 50 interrupts either optical interrupter 108 as described above.

Figure 5:
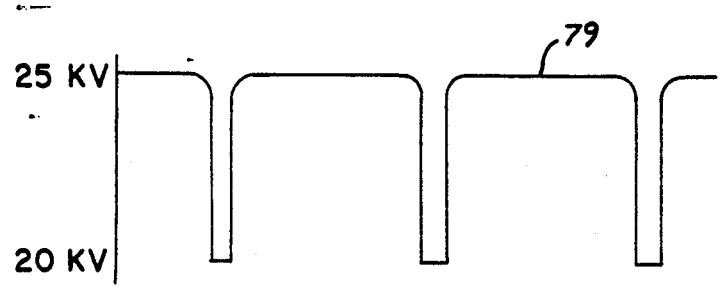
FIG. 5 is a diagram showing the modulation of the x-ray beam with respect to the grid positions indicated in FIG. 4 and according to one embodiment of the invention.

Referring now to FIG. 5, the x-ray fan beam 24 is modulated as indicated by waveform 79 such that the beam 24 is decreased in intensity during the period that the grid 30 is changing directions and fully on for the remainder of the grid movement. In the first embodiment, this modulation is the result of the blocking of the x-ray beam by the chopper wheel 18. In the second embodiment, the x-ray beam 24 is modulated by varying the x-ray tube voltage between approximately 25 and 20 KVP. The percentage of time the x-ray beam is at full strength will be termed the "beam duty cycle".

The required beam duty cycle will depend on the time needed to reverse the grid 30 direction, which in turn depends chiefly on the strength of the reciprocation motor 62, the mass of the grid 30, and the rigidity of the mechanical linkage between the two including the reciprocation arm 48, the track 52 and the racks 56 and pinions and pinion drive shaft 58 and 60. As mentioned above, a 95% duty cycle has been used successfully to eliminate grid lines.

As has been discussed, the grid 30 moves longitudinally, by a distance equal to the width of the fan beam 24, during the time required for one grid reciprocation cycle. It will be apparent therefor that the reduction of exposure occurring from modulation of the x-ray beam, at the end of grid reciprocation travel, will be distributed evenly over the surface of the x-ray sensitive medium with the scanning of the fan beam 24 in the longitudinal direction.

A preferred embodiment of the invention has been described, but it should be apparent to those skilled in the art that many variations can be made without departing from the spirit of the invention. For example, the modulation of the x-ray beam need not be between two values. A modulation waveform made proportional to the absolute velocity of grid could be used to provide extremely flat exposure curves under a variety of grid motion patterns. It will be apparent, also that this modulation technique is equally applicable to non-scanning x-ray systems, such as area beam systems, as well as those x-ray systems that scan in a different manner than that described herein.

I claim:

1. A diagnostic x-ray machine for producing a radiographic image of a body, said image received by an x-ray sensitive medium, comprising:
   an x-ray source for producing a beam of x-ray radiation along a major axis directed through the body and toward the x-ray sensitive medium;
   a grid means positioned relative to the x-ray source, within the beam of x-rays after they pass through the body but prior to their reaching the x-ray sensitive medium, for rejecting the x-rays scattered by the body;
   a reciprocating means for moving the grid means along an axis perpendicular to the major axis between a first limit and a second limit;
   a modulator means for controlling the intensity of the x-ray beam from the x-ray source; and
   a signal means for synchronizing the modulator means with the motion of the grid means between the first and second limit so as to control x-ray intensity as a function of grid velocity.

2. The diagnostic x-ray machine of claim 1 wherein the reciprocating means moves the grid at substantially constant velocity while the grid is greater than a first predetermined distance from the first limit and greater than a second predetermined distance from the second limit and wherein the signal means produces a signal when the grid is less than a first predetermined distance from the first limit or less than a second predetermined distance from the second limit and the modulator means reduces the intensity of the x-ray beam when it receives this signal.

3. The diagnostic x-ray machine of claim 2 wherein the first and second predetermined distances are equal to the distance required for the deceleration and acceleration associated with grid direction reversal.

4. The diagnostic x-ray machine of claim 1 wherein the modulator means reduces the x-ray beam when the grid is less than a first predetermined distance from the first limit or less than a second predetermined distance from the second limit.

5. The diagnostic x-ray machine of claim 1 wherein the modulator is comprised of a chopper wheel for obstructing and passing the x-ray beam.

6. The diagnostic x-ray machine of claim 1 wherein the x-ray beam intensity is a function of x-ray tube voltage and wherein the modulator means controls the x-ray tube voltage.

7. A diagnostic x-ray machine for producing a radiographic image of a body, said image received by an x-ray sensitive medium, comprising:
  an x-ray source for producing a beam of x-ray radiation along a major axis directed through the body and toward the x-ray sensitive medium;
  a grid means positioned relative to the x-ray source, within the beam of x-rays after they pass through the body but prior to their reaching the x-ray sensitive medium, for rejecting the x-rays scattered by the body;
  a reciprocating means for moving the grid means along an axis perpendicular to the major axis between a first limit and a second limit;
  a modulator means for controlling the intensity of the x-ray beam from the x-ray source comprising a chopper wheel for obstructing and passing the x-ray beam; and
  a signal means for synchronizing the modulator means with the motion of the grid means between the first and second limit.

8. A diagnostic fan beam x-ray machine for producing a radiographic image of a body, said image received by an x-ray sensitive medium, comprising:
  an x-ray source for producing a fan beam of x-ray radiation along a major axis directed through the body and toward an x-ray sensitive medium, and including a scanning means for sweeping the fan beam in longitudinal direction;
  a grid means positioned relative to the x-ray source for rejecting the x-rays scattered by the body after they pass though the body but prior to their reaching the x-ray sensitive medium;
  a grid translation means for moving the grid in the longitudinal direction so as to be positioned within the fan beam at all times during the sweep of the fan beam;
  a reciprocating means for moving the grid means in a transverse direction along an axis perpendicular to the major axis between a first limit and a second limit so that the grid completes at least one cycle of reciprocation in the time required for the grid to translate the width of the fan beam in the longitudinal direction;
  a modulator means for controlling the intensity of the x-ray beam from the x-ray source; and
  a signal means for synchronizing the modulator means with the motion of the grid means between the first and second limit.

* * * * *